United States Patent
Popovic et al.

(10) Patent No.: US 11,413,099 B2
(45) Date of Patent: *Aug. 16, 2022

(54) SYSTEM, CONTROLLER AND METHOD USING VIRTUAL REALITY DEVICE FOR ROBOTIC SURGERY

(71) Applicant: KONINKLIJKE PHILIPS N.V., Eindhoven (NL)

(72) Inventors: Aleksandra Popovic, Boston, MA (US); David Paul Noonan, New York, NY (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 135 days.

This patent is subject to a terminal disclaimer.

(21) Appl. No.: 16/871,645

(22) Filed: May 11, 2020

(65) Prior Publication Data

US 2020/0268462 A1 Aug. 27, 2020

Related U.S. Application Data

(63) Continuation of application No. 16/065,928, filed as application No. PCT/EP2016/082716 on Dec. 27, 2016, now Pat. No. 10,646,289.

(Continued)

(51) Int. Cl.
*A61B 34/30* (2016.01)
*A61B 34/00* (2016.01)
(Continued)

(52) U.S. Cl.
CPC .............. *A61B 34/30* (2016.02); *A61B 34/20* (2016.02); *A61B 34/25* (2016.02); *G06F 3/012* (2013.01);
(Continued)

(58) Field of Classification Search
CPC ......... A61B 34/30; A61B 34/20; A61B 34/25; A61B 34/74; A61B 2034/2057;
(Continued)

(56) References Cited

U.S. PATENT DOCUMENTS 5,641,288 A 6/1997 Zaenglein
5,876,325 A * 3/1999 Mizuno ................... A61B 34/37
  600/117

(Continued)

FOREIGN PATENT DOCUMENTS

CN 111801704 A * 10/2020 ......... A61B 1/00009
EP 2169346 3/2010

(Continued)

OTHER PUBLICATIONS

"Surgical and interventional robotics: part III;" Gregory D. Hager, Allison M. Okamura, Peter Kazanzides, Louis L. Whitcomb, Gabor Fichtinger, Russell H. Taylor; IEEE Robotics & Automation Magazine (vol. 15, Issue: 4, pp. 84-93); Jan. 16, 2009. (Year: 2009).*

(Continued)

*Primary Examiner* — Khoi H Tran
*Assistant Examiner* — Jorge O Peche

(57) ABSTRACT

A control unit is provided for a surgical robot system, including a robot configured to operate an end-effector in a surgical site of a patient. The control unit includes a processor configured to transmit acquired live images of a patient, received from an image acquisition device, to a virtual reality (VR) device for display; to receive input data from the VR device, including tracking data from a VR tracking system of the VR device based on a user's response to the live images displayed on a viewer of the display unit of the VR device; to process the input data received from the VR device to determine a target in the patient; to determine a path for the end-effector to reach the target based upon the (Continued)

live images and the processed input data; and to transmit control signals to cause the robot to guide the end-effector to the target via the determined path.

22 Claims, 6 Drawing Sheets

Related U.S. Application Data

(60) Provisional application No. 62/272,512, filed on Dec. 29, 2015.

(51) Int. Cl.
*A61B 34/20* (2016.01)
*G06F 3/01* (2006.01)

(52) U.S. Cl.
CPC .............. *G06F 3/013* (2013.01); *A61B 34/74* (2016.02); *A61B 2034/2057* (2016.02); *A61B 2034/254* (2016.02); *A61B 2034/301* (2016.02); *A61B 2034/306* (2016.02)

(58) Field of Classification Search
CPC ........ A61B 2034/254; A61B 2034/301; A61B 2034/306; G06F 3/012; G06F 3/013
See application file for complete search history.

(56) References Cited

U.S. PATENT DOCUMENTS

| | | | |
|---|---|---|---|
| 6,139,490 A | 10/2000 | Breidenthal | |
| 6,459,926 B1 | 10/2002 | Blumenkranz | |
| 6,847,336 B1 * | 1/2005 | Lemelson | H04N 7/147 345/8 |
| 8,396,598 B2 | 3/2013 | Fieding | |
| 8,878,900 B2 | 11/2014 | Lerotic | |
| 9,095,252 B2 | 8/2015 | Popovic | |
| 9,538,962 B1 * | 1/2017 | Hannaford | G16H 40/63 |
| 9,844,321 B1 * | 12/2017 | Ekvall | A61B 90/37 |
| 9,861,446 B2 * | 1/2018 | Lang | H05K 999/99 |
| 9,898,662 B2 * | 2/2018 | Tsuda | G02B 27/017 |
| 9,916,691 B2 * | 3/2018 | Takano | G02B 27/0093 |
| 10,034,508 B2 * | 7/2018 | Frank | G02B 27/0176 |
| 10,042,598 B2 * | 8/2018 | Tsuda | G06F 3/1423 |
| 10,134,185 B2 * | 11/2018 | Kihara | G06F 3/012 |
| 10,154,239 B2 * | 12/2018 | Casas | H04N 13/111 |
| 10,416,769 B2 | 9/2019 | Ofek | |
| 10,499,997 B2 * | 12/2019 | Weinstein | A61F 2/461 |
| 10,571,671 B2 * | 2/2020 | Hirayama | A61B 1/00149 |
| 10,646,283 B2 * | 5/2020 | Johnson | G02B 27/017 |
| 10,702,353 B2 * | 7/2020 | Tesar | H04N 5/23293 |
| 10,786,319 B2 * | 9/2020 | Popovic | A61B 34/30 |
| 10,791,924 B2 * | 10/2020 | Toth | A61B 5/486 |
| 10,838,210 B2 * | 11/2020 | Robaina | B60K 35/00 |
| 10,861,236 B2 * | 12/2020 | Geri | G02B 27/0172 |
| 10,898,276 B2 * | 1/2021 | Graetzel | A61B 34/30 |
| 10,898,286 B2 * | 1/2021 | Srinivasan | A61B 34/20 |
| 10,908,681 B2 * | 2/2021 | Meglan | G02B 27/017 |
| 10,912,625 B2 * | 2/2021 | Browd | G06T 19/20 |
| 10,966,798 B2 * | 4/2021 | Tesar | G16H 20/40 |
| 10,973,625 B2 * | 4/2021 | Ma | G02B 1/002 |
| 10,987,174 B2 * | 4/2021 | Draper | A61B 34/30 |
| 10,987,176 B2 * | 4/2021 | Poltaretskyi | A61B 17/15 |
| 11,045,269 B2 * | 6/2021 | Sachs | B25J 9/108 |
| 11,071,592 B2 * | 7/2021 | McGuan | A61B 5/1072 |
| 11,172,990 B2 * | 11/2021 | Lang | A61B 17/1703 |
| 11,176,750 B2 * | 11/2021 | Jones | G06T 19/006 |
| 2006/0028400 A1 | 2/2006 | Lapstun | |
| 2012/0307027 A1 | 12/2012 | Popovic | |
| 2013/0030571 A1 | 1/2013 | Ruiz Morales | |
| 2013/0063580 A1 | 3/2013 | Ogawa | |
| 2014/0163359 A1 | 6/2014 | Frimer | |
| 2014/0275760 A1 | 9/2014 | Choi | |
| 2014/0303643 A1 | 10/2014 | Byung | |
| 2016/0170488 A1 | 6/2016 | Hanamoto | |
| 2016/0225192 A1 | 8/2016 | Jones | |
| 2017/0059871 A1 | 3/2017 | Hashiba | |
| 2017/0155736 A1 | 6/2017 | Schukovets | |
| 2017/0258526 A1 | 9/2017 | Lang | |
| 2017/0307333 A1 | 10/2017 | Northrup | |
| 2018/0204380 A1 | 7/2018 | Kumar | |
| 2018/0356880 A1 | 12/2018 | Kashihara | |
| 2019/0029765 A1 | 1/2019 | Crawford | |
| 2019/0155384 A1 | 5/2019 | Fajt | |
| 2019/0353457 A1 | 11/2019 | Northrup | |
| 2020/0268462 A1 * | 8/2020 | Popovic | A61B 34/25 |

FOREIGN PATENT DOCUMENTS

| | | | |
|---|---|---|---|
| EP | 2996622 | * | 7/2020 |
| JP | 2019503766 | * | 2/2019 |
| JP | 2019512315 | * | 5/2019 |
| WO | 2015143067 | | 9/2015 |

OTHER PUBLICATIONS

"Human-computer interfaces for interaction with surgical tools in robotic surgery;" Staub, C., Can, S. , Jensen, B., Knoll, A. , Kohlbecher, S.; 2012 4th IEEE RAS & EMBS International Conference on Biomedical Robotics and Biomechatronics (BioRob) (pp. 81-86); Jun. 1, 2012. (Year: 2012).*

Noonan, et al: "Gaze Contingent Articulated Robot Control for Robot Assisted Minimally Invasive Surgery", IEEE 2008.

Tong, et al: "A Retrofit Eye Gaze Tracker for the da Vinci and its Integration in Task Execution using the da Vinci Research Kit", 2015 IEEE.

* cited by examiner

SYSTEM, CONTROLLER AND METHOD USING VIRTUAL REALITY DEVICE FOR ROBOTIC SURGERY

CROSS-REFERENCE TO PRIOR APPLICATIONS

This application is a continuation of U.S. patent application Ser. No. 16/065,928 filed on Jun. 25, 2018, which is the U.S. National Phase application under 35 U.S.C. § 371 of International Application No. PCT/EP2016/082716, filed on Dec. 27, 2016, which claims the benefit of U.S. Provisional Patent Application No. 62/272,512 filed on Dec. 29, 2015. These applications are hereby incorporated by reference herein.

TECHNICAL FIELD

The present approach relates to the field of surgery, in particular to a system, controller and method for control of a robot having a rigid proximal portion and a flexible distal portion using medical imagery and tracking data from a virtual reality device.

BACKGROUND

Surgery generally relies on individual skills of surgeons. Dexterity typically is limited to a surgeon's hands and rigid instruments. These limitations are particularly apparent in minimally invasive surgery or natural orifice surgery, in which space to operate is confined by entry point and by anatomy. In minimally invasive surgery, visual feedback is usually provided by an endoscope.

Surgical robots and/or steerable devices may be used in minimally invasive surgery to improve the surgeon's dexterity inside the patient at a surgical site. Examples of surgical robots include multi-arm systems, such as da Vinci® robots, or flexible robots, such as Medrobotics Flex® robotic systems. These robotic systems are controlled by the surgeon (or user) using different interface mechanisms, including hand controllers or input handles for the operating robotic systems, and image displays for capturing endoscope video and displaying various control modes of the robotic systems.

Control of hand-held dexterous devices is challenging. The user has to combine the motion of non-dexterous proximal end which is usually around a fulcrum point (entry point to the body) and complex dexterous motion inside the body. An approach to this problem is robotic positioning of the dexterous device which increases footprint in the operating room and increases cost and duration of surgery. This problem is amplified if the proximal end is not within field-of-view of imaging devices (e.g. an endoscope takes images only on the inside of the patient, and the field of view in a portable imaging system, such as a C-arm, is too small to take image of the entire device and can cause radiation exposure to the operator). In addition, once the position is achieved with the dexterous device, hand tremors and involuntary motion of the hand can cause mis-alignment. In order to improve the surgeon's dexterity, surgical robots may have more than six degrees of freedom, making them unintuitive and otherwise difficult to control.

This issue is amplified by operation in constrained spaces, such as those encountered during minimally invasive surgery or natural orifice surgery and by use of hyper-redundant robots, such as snake robots. Control of these robots is usually performed using handles that are complex to operate and are usually associated with steep learning curve. Users are using endoscope images to navigate the surgical field and it is difficult to map the motion of the handle with the images.

Accordingly, it is desirable to provide an apparatus, systems, methods, and computer-readable storage media for control of a surgical robot using a combination of live imagery and tracking information provided from a virtual reality device enabling target selection using motion detection, while not depending on use of the user's hands or dexterity, generally.

SUMMARY

According to an illustrative embodiment, a control unit for a surgical robot system, including a robot configured to operate at least one end-effector in a surgical site of a patient, includes a processor. The processor is configured to transmit acquired live images of a patient, received from at least one image acquisition device, to a virtual reality (VR) device for display on a display unit; to receive input data from the VR device, the input data including tracking data from a VR tracking system of the VR device based on a user's response to the acquired live images of the patient displayed on the display unit of the VR device; to process the input data received from the VR device to determine a target in the patient; to determine a path for the at least one end-effector operable by the robot to reach the target based upon the acquired live images and the processed input data; and to transmit robot control signals to cause the robot to guide the at least one end-effector to the target via the determined path.

According to another illustrative embodiment, a surgical robot system includes a robot configured to operate at least one end-effector positioned at a surgical site within a patient; at least one image acquisition device configured to acquire live images at the surgical site; a virtual reality (VR) device configured to display the acquired live images and determine tracking data provided by actions of a user via the VR device; and a control unit comprising input/output (I/O) circuitry and a processor. The I/O circuitry is configured to receive the acquired live images from the at least one image acquisition device, to provide the acquired live images to the VR device for display, to receive the determined tracking data from the VR device, and to provide robot control signals to the robot. The processor is configured to transmit the acquired live images, received from the at least one image acquisition device via the I/O circuitry, to the VR device; to process the determined tracking data from the VR device to select a target at the surgical site within the patient; to determine a path for the at least one end-effector to reach the selected target based upon the acquired live images and the processed determined tracking data; and to transmit the robot control signals to the robot to move the at least one instrument to the selected target via the determined path.

According to another illustrative embodiment, a non-transitory computer-readable storage medium storing machine readable instructions executable by a processor to operate a surgical robot system is provided. The surgical robot system includes at least one robot configured to operate at least one end-effector to be positioned at a surgical site within a patient, at least one image acquisition device configured to acquire live images at the surgical site, and a head-mounted display (HMD) device to be worn by a user and configured to display the acquired live images and to determine at least one of motion of the user's head or movement of the user's eyes. The non-transitory computer readable medium includes transmitting code for causing transmission of the acquired live images, received from the at least one image acquisition device, to the HMD device; processing code for processing determined at least one of head-tracking data and eye-tracking data from the HMD device to select a target at the surgical site within the patient; determining code for determining a path for a distal portion of the robot, including the at least one end-effector, to reach the selected target at the surgical site within the patient based upon the acquired live images and the processed determined head-tracking data and/or eye-tracking data; and robot control code for causing transmission of the robot control signals to the robot to move the at least one end-effector to the selected target at the surgical site within the patient via the determined path.

BRIEF DESCRIPTION OF THE DRAWINGS

The present invention will be more readily understood from the detailed description of exemplary embodiments presented below considered in conjunction with the accompanying drawings, as follows.

DETAILED DESCRIPTION

Figure 1:
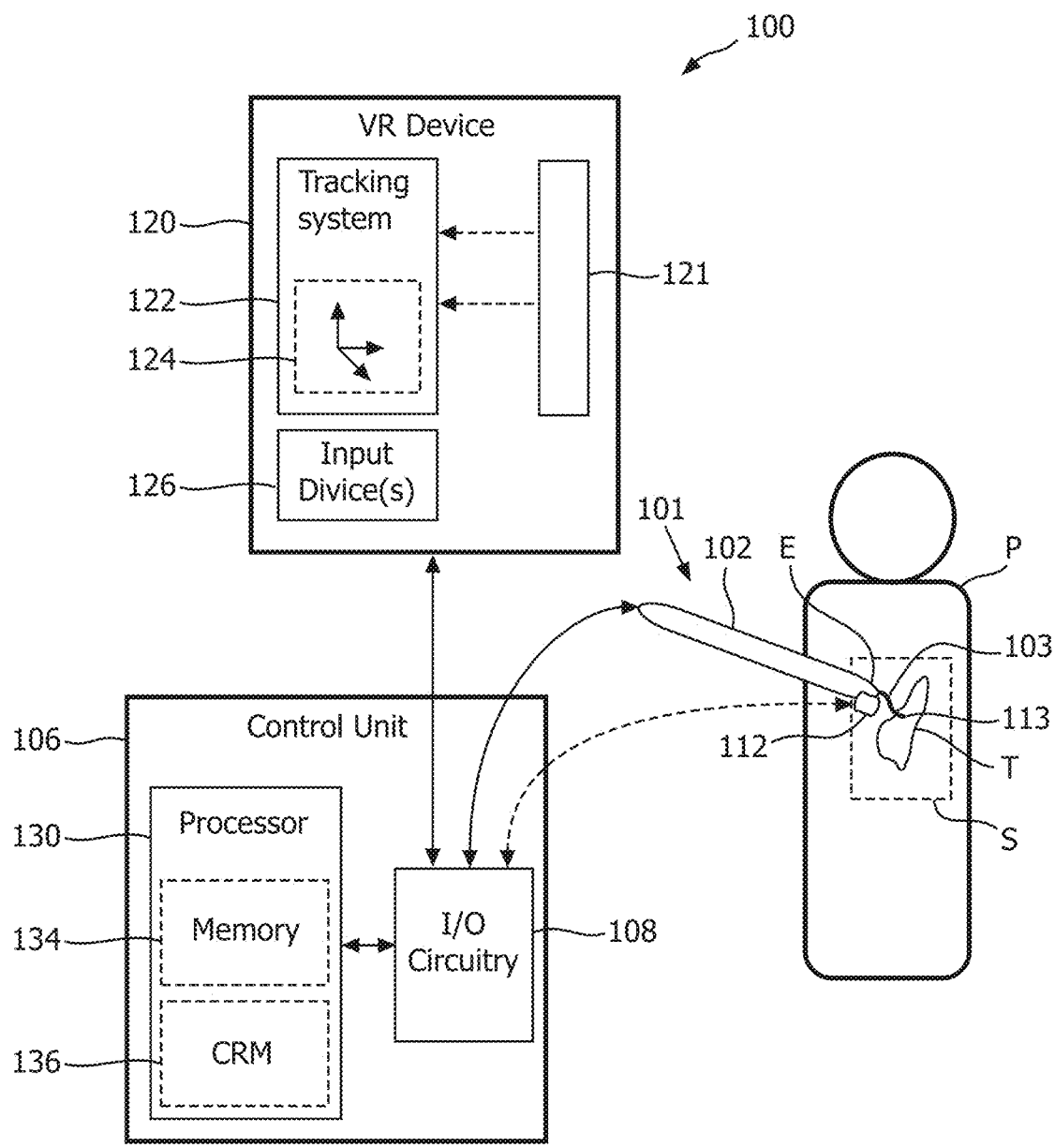
FIG. 1 is a schematic block diagram showing a surgical robot system, in accordance with an illustrative embodiment of the present invention.

The present invention will now be described more fully hereinafter with reference to the accompanying drawings, in which embodiments of the present invention are shown. The present invention may, however, be embodied in different forms and should not be construed as limited to the embodiments set forth herein. Rather, these embodiments are provided as teaching examples of the invention.

Generally, according to various embodiments, a virtual reality (VR) device is provided that a user (e.g., a surgeon) uses to control a robot through physical movement by the surgeon (e.g., other than use of the user's hands to manipulate conventional manual controls) to identify and select a target for the robot based on live images received by the VR device. The live images may be endoscopic images, for example, by a camera mounted to the distal end of an endoscopic, e.g., which may be operable by a dedicated endoscope controller, or by a forward-looking camera, e.g., which may be operable by the robot). For example, the VR device may be a head-mounted display (HMD) device that displays an endoscopic image on a display in a head piece worn by the user showing the surgical site, e.g., inside a patient. The HMD device further includes one or more sensors configured to detect motion of the user, such as head motion or eye movement, where the detected motion is processed to select the target in the surgical site, shown in the image on the display, for the robot. Using the live images and the head motion and/or eye movement detection improves usability of the robot by simulating experience during conventional surgery, where the surgeon moves his or her head and/or directs eye movement toward the area (target) on which the surgeon is focused, while preserving improved dexterity of a surgical robot.

It is to be understood that the terminology used herein is for purposes of describing particular embodiments only, and is not intended to be limiting. Any defined terms are in addition to the technical and scientific meanings of the defined terms as commonly understood and accepted in the technical field of the present teachings.

As used in the specification and appended claims, the terms "a", "an" and "the" include both singular and plural referents, unless the context clearly dictates otherwise. Thus, for example, "a device" includes one device and plural devices.

As used herein, the statement that two or more parts or components are "coupled" shall mean that the parts are joined or operate together either directly or indirectly, i.e., through one or more intermediate parts or components, so long as a link occurs.

Directional terms/phrases and relative terms/phrases may be used to describe the various elements" relationships to one another, as illustrated in the accompanying drawings. These terms/phrases are intended to encompass different orientations of the device and/or elements in addition to the orientation depicted in the drawings.

A "computer-readable storage medium" as used herein encompasses any tangible storage medium which may store instructions which are executable by a processor of a computing device. The computer-readable storage medium may be referred to as a non-transitory computer-readable storage medium, to distinguish from transitory media such as transitory propagating signals. The computer-readable storage medium may also be referred to as a tangible computer-readable medium.

In some embodiments, a computer-readable storage medium may also be able to store data which is able to be accessed by the processor of the computing device. Examples of computer-readable storage media include, but are not limited to: a floppy disk, a magnetic hard disk drive, a solid state hard disk, flash memory, a USB thumb drive, Random Access Memory (RAM), Read Only Memory (ROM), an optical disk, a magneto-optical disk, and the register file of the processor. Examples of optical disks include Compact Disks (CD) and Digital Versatile Disks (DVD), for example CD-ROM, CD-RW, CD-R, DVD-ROM, DVD-RW, or DVD-R disks. The term computer readable-storage medium also refers to various types of recording media capable of being accessed by the computer device via a network or communication link. For example a data may be retrieved over a modem, over the internet, or over a local area network. References to a computer-readable storage medium should be interpreted as possibly being multiple computer-readable storage mediums. Various executable components of a program or programs may be stored in different locations. The computer-readable storage medium may for instance be multiple computer-readable storage medium within the same computer system. The computer-readable storage medium may also be computer-readable storage medium distributed amongst multiple computer systems or computing devices.

"Memory" is an example of a computer-readable storage medium. Computer memory is any memory which is directly accessible to a processor. Examples of computer memory include, but are not limited to RAM memory, registers, and register files. References to "computer memory" or "memory" should be interpreted as possibly being multiple memories. The memory may for instance be multiple memories within the same computer system. The memory may also be multiple memories distributed amongst multiple computer systems or computing devices.

Computer storage is any non-volatile computer-readable storage medium. Examples of computer storage include, but are not limited to: a hard disk drive, a USB thumb drive, a floppy drive, a smart card, a DVD, a CD-ROM, and a solid state hard drive. In some embodiments computer storage may also be computer memory or vice versa. References to "computer storage" or "storage" should be interpreted as possibly including multiple storage devices or components. For instance, the storage may include multiple storage devices within the same computer system or computing device. The storage may also include multiple storages distributed amongst multiple computer systems or computing devices.

A "processor" as used herein encompasses an electronic component which is able to execute a program or machine executable instruction. References to the computing device comprising "a processor" should be interpreted as possibly containing more than one processor or processing core. The processor may for instance be a multi-core processor. A processor may also refer to a collection of processors within a single computer system or distributed amongst multiple computer systems. The term computing device should also be interpreted to possibly refer to a collection or network of computing devices each comprising a processor or processors. Many programs have instructions performed by multiple processors that may be within the same computing device or which may even be distributed across multiple computing devices.

A "user interface" or "user input device" as used herein is an interface which allows a user or operator to interact with a computer or computer system. A user interface may provide information or data to the operator and/or receive information or data from the operator. A user interface may enable input from an operator to be received by the computer and may provide output to the user from the computer. In other words, the user interface may allow an operator to control or manipulate a computer and the interface may allow the computer indicate the effects of the user's control or manipulation. The display of data or information on a display or a graphical user interface is an example of providing information to an operator. The receiving of data through a touch screen, keyboard, mouse, trackball, touchpad, pointing stick, graphics tablet, joystick, gamepad, webcam, headset, gear sticks, steering wheel, wired glove, wireless remote control, and accelerometer are all examples of user interface components which enable the receiving of information or data from a user.

A "hardware interface" as used herein encompasses an interface which enables the processor of a computer system to interact with and/or control an external computing device and/or apparatus. A hardware interface may allow a processor to send control signals or instructions to an external computing device and/or apparatus. A hardware interface may also enable a processor to exchange data with an external computing device and/or apparatus. Examples of a hardware interface include, but are not limited to: a universal serial bus, IEEE 1394 port, parallel port, IEEE 1284 port, serial port, RS-232 port, IEEE-488 port, Bluetooth connection, Wireless local area network connection, TCP/IP connection, Ethernet connection, control voltage interface, MIDI interface, analog input interface, and digital input interface.

A "display" or "display device" or "display unit" as used herein encompasses an output device or a user interface adapted for displaying images or data. A display may output visual, audio, and or tactile data. Examples of a display include, but are not limited to: a computer monitor, a television screen, a touch screen, tactile electronic display, Braille screen, Cathode ray tube (CRT), Storage tube, Bistable display, Electronic paper, Vector display, Flat panel display, Vacuum fluorescent display (VF), Light-emitting diode (LED) displays, Electroluminescent display (ELD), Plasma display panels (PDP), Liquid crystal display (LCD), Organic light-emitting diode displays (OLED), a projector, and Head-mounted display.

Like numbered elements in these figures are either equivalent elements or perform the same function. Elements which have been discussed previously will not necessarily be discussed in later figures if the function is equivalent.

Initially, it is noted that medical images may include 2D or 3D images such as those obtained via an endoscopic camera provided on a distal end of an endoscope, or via a forward-looking camera provided at the distal end of a robot (e.g. as the end effector). Also, live images may include still or video images captured through medical imaging during the minimally invasive procedure. Other medical imaging may be incorporated during the surgical process, such as images obtained by, X-ray, ultrasound, and/or magnetic resonance, for example, for a broader view of the surgical site and surrounding areas.

FIG. 1 is a schematic block diagram showing a surgical robot system, in accordance with a representative embodiment of the present invention. FIG. 1 depicts surgical robot system 100, which may be utilized for medical procedures, typically involving manipulation of surgical instruments and other tools operable by a robot at a surgical site located within a patient's body. Such medical procedures include, but are not limited to, minimally invasive cardiac surgery (e.g., coronary artery bypass grafting or mitral valve replacement), minimally invasive abdominal surgery (laparoscopy) (e.g., prostatectomy or cholecystectomy), and natural orifice translumenal endoscopic surgery, for example.

Referring to FIG. 1, in the depicted embodiment, the surgical robot system 100 includes at least one robot 101, a control unit 106, and a virtual reality (VR) device 120. The robot 101 is configured to operate one or more end-effectors to be positioned at a surgical site S within a patient P, including at least one image acquisition device 112 configured to acquire live images at the surgical site S and at least one instrument 113, such has a surgical tool for performing an internal surgical procedure. Internal surgical procedures may include minimally invasive surgeries or natural orifice surgeries, for instance, involving an anatomical target T within the surgical site S, examples of which are mentioned above.

The VR device 120 is configured to display the acquired live images on a VR display unit 121 to be viewed by the user, and to detect tracking data using a VR tracking system 122 that captures the user's movements (responsive to the displayed images) via one or more motion sensing circuits, indicated by representative motion sensor 124. For example, as discussed further below, the VR device 120 may be a head mounted display (HMD) device including a head piece worn by the user that includes the display unit 121 and the motion sensor 124. The display unit 121 may be a single display or it may be divided into two eye displays (not shown), corresponding to the eyes of the user. The two eye displays enable three-dimensional viewing when the image acquisition device 112 is stereoscopic or pseudo three-dimensional viewing when the image acquisition device 112 is monocular, but the two eye displays are configured to partially overlap. The motion sensor 124 may be multiple accelerometers, for example, for detecting motion of the user's head around three axes, such that the tracking data comprises head-tracking data corresponding to head movements of the user. Alternatively, the motion sensor 124 may include backward facing camera(s) for detecting movement of the user's eyes, such that the tracking data comprises eye-tracking data corresponding to eye movements of the user.

The VR device 120 also may include one or more input devices (e.g. user interfaces), indicated by input device 126, for receiving instructions from the user. The input device 126 as used herein is an interface which allows the user to interact with the VR device 120, as well as the surgical robot system 100. The input device 126 may include one or more of a touch screen, keyboard, mouse, trackball, touchpad, or voice command interface, for example. In the present embodiment, the user may use the input device 126 to enter specific commands, such as sending an acknowledgment signal to the processor 130 to confirm a selected target T as determined by the processor 130, or to send an activation signal to the VR tracking system 122 and/or the processor 130 to activate one of a head-tracking mode that includes the detection of the head motion by the HMD device or an eye-tracking mode that includes the detection of the eye movements by the HMD device. In alternative embodiments, the input device 126 may be outside the VR device 120. For example, the input device 126 may be integrated into the control unit 106 or may be a separate unit configured to communicate with both the VR device 120 and the processor 130 via the I/O circuitry 108.

The control unit 106 is configured to control and otherwise coordinate overall operations of the surgical robot system 100. The control unit 106 includes input/output (I/O) circuitry 106 and a processor 130. The processor 130 includes associated memory 134 for enabling the processing and computer readable medium (CRM) 136. The processor 130 is generally configured to receive the acquired live images from the image acquisition device 112 via the I/O circuitry 108, and to process and store the acquired live images, e.g., in the memory 134 and/or the CRM 136, so that the processor 130 is able to build a database essentially visually mapping interior portions of the patient P traversed by the image acquisition device 112. This database may be used subsequently to determine a path to the target T, once the target T has been selected, as discussed below. The processor 130 transmits the acquired live images to the VR device 120 via the I/O circuitry 108 for display on the display unit 121. In alternative configurations, the acquired live images may be transmitted to the VR device 120 from the I/O circuitry 108 upon receiving the acquired live images by the I/O circuitry 108, without any imaging processing performed by the processor 130.

The processor 130 is further configured to receive tracking data to determine by the VR tracking system 122 from the VR device 120 via the I/O circuitry 108, and to process the determined tracking data to select a target (e.g., the target T) at the surgical site S within the patient P. The processor 130 is further configured to determine a path for the one or more end-effectors of the robot 101, e.g., including the illustrative image acquisition device 112 and instrument 113, to reach the selected target T based upon the acquired live images and the processed determined tracking data. The processor 130 transmits robot control signals to the robot 101 via the I/O circuitry 108 to move the one or more end-effectors to the selected target T along the determined path.

Accordingly, the I/O circuitry 108 receives the acquired live images from the image acquisition device 112, and provides the acquired live images to the processor 130 and/or to the VR device 120 (either directly or forwarded from the processor 130 after image processing) for display on the display unit 121. The I/O circuitry 108 also receives the input data (including tracking data) from the VR device 120, which it provides to the processor 130, and sends robot control signals determined by the processor 130 in response to the tracking data to the robot 101.

In the depicted embodiment, the robot 101 has a rigid proximal portion 102 (e.g., a robot arm or a portion of a robot arm) to be positioned at an entry point E in the body of the patient P, and a flexible distal portion 103 to be positioned at a surgical site S within the patient P. The robot 101 is broadly defined herein as any robotic device structurally configured with motorized control of one or more joints and two or more corresponding links for maneuvering the flexible distal portion 103 as desired for the particular robotic procedure. The flexible distal portion 103 may include one or more end-effectors, including the image acquisition device 112 and the instrument 113. The instrument 113 may be a gripper or a tool holder, a laparoscopic instrument, laparoscope, a tool for screw placement, e.g., in spinal fusion surgery, a needle for biopsy or therapy, an ultrasonic transducer for tissue or tumor imaging and ablation, or other surgical or interventional tool, for example.

In practice, as would be appreciated by those skilled in the art, the robot 101 may have a minimum of three (3) degrees-of-freedom, and beneficially six (6) or more degrees-of-freedom. The robot 101 may have a remote center of motion (RCM) mechanism with two intersecting motor axes. Also, the robot 101 may have associated therewith a light projection apparatus (not shown). An example of a steerable or dexterous surgical robotic device which may be incorporated is a seven-degree of freedom universal wrist, such as described by Sanchez, U.S. Pat. No. 7,121,781 (Oct. 17, 2006), which is hereby incorporated by reference. The universal wrist includes multiple joints and jaws at the distal portion, and the drive system at the proximal portion. The device can further be positioned using a robotic positioner and computer controller. The robotic positioning allows for tracking of the device motion with respect to anatomy. An end-effector may be coupled to the wrist, which provides two separate degrees of freedom about the same pivot point. The end-effector can be moved and actuated by pins, allowing for a compact minimally invasive medical instrument.

Although a single robot 101 for operating a single rigid proximal portion 102 and a single corresponding distal portion 103 is depicted in FIG. 1, it is understood that multiple robots with corresponding multiple rigid proximal portions and/or multiple rigid distal portions may be incorporated without departing from the scope of the present teachings. That is, the robot 101 may include multiple robotic arms (not shown) controlling different end-effectors in the surgical site S. For example, one robotic arm may include a forward-looking camera, such as the image acquisition device 112 for providing the live images of the surgical site S, while another robotic arm may include the instrument 113, as well as additional instrument(s).

The image acquisition device 112 defines part of an imaging system with control unit 106 of the surgical robot system 100, and may include one or more of any type of camera having a forward optical view or an oblique optical view, and may be capable of acquiring a sequence of two-dimensional digital video frames at a predefined frame rate (e.g., 30 frames per second) and capable of providing each digital video frame to the control unit 106 via the input/output circuitry 108. In particular, image acquisition device 112 may be a forward-looking camera positioned and oriented such that within its field of view it can acquire live images of the surgical site S and the anatomical target T (e.g. an organ) from the flexible distal portion 103 of the robot 101. In an embodiment, the rigid proximal portion 102 may be an endoscope like device controlled by the robot 101, where the single proximal portion 102 includes multiple channels, one of which enables control of and/or communication with the image acquisition device 112 and at least one other of which enables entry and control of the instrument 113 or other end-effectors. In alternative embodiments, the image acquisition device 112 is in the flexible distal portion 103 corresponding to the rigid proximal portion 102, while other end-effectors may be in flexible distal portions corresponding to other rigid proximal portions (not shown), all of which are controlled via the robot 101. In yet another embodiment, the image acquisition device 112 is in the flexible distal portion of a separate endoscope, not part of the robot 101, but rather under control of a separate endoscope controller (operating in conjunction with the robot 101), as discussed below with reference to FIG. 2. Also, the image acquisition device 112 may be a stereoscopic camera or stereoscopic endoscope that provides images that can be perceived in three dimensions. An example of a stereoscopic endoscope is described by Breidenthal et al., U.S. Pat. No. 6,139,490 (Oct. 31, 2000), which is hereby incorporated by reference. Alternatively, the image acquisition device 112 may be monocular and the display unit 121 is divided into two eye displays corresponding to the user's eyes, in which case, the monocular image is split in two overlapping halves and presented on each of the two eye displays separately to create a pseudo-stereo view.

An external medical imagery device may also be included. The medical imagery device may be configured to acquire a live image or live images of the flexible distal portion 103 of the surgical robot 101 and the target T at the surgical site S, providing a more comprehensive overview. Such a medical imagery device may include a C-arm (not shown) at least partially surrounding a portion of the patient P. A C-arm an imaging scanner intensifier, so named because of its C shaped configuration. C-arms have radiographic capabilities, and may be used for fluoroscopic imaging during surgical procedures, as is known to those skilled in the art. An example of a C-arm, implementing an X-ray system, is described by Popovic, U.S. Pat. No. 9,095,252 (Aug. 4, 2015), which is hereby incorporated by reference.

Figure 2:
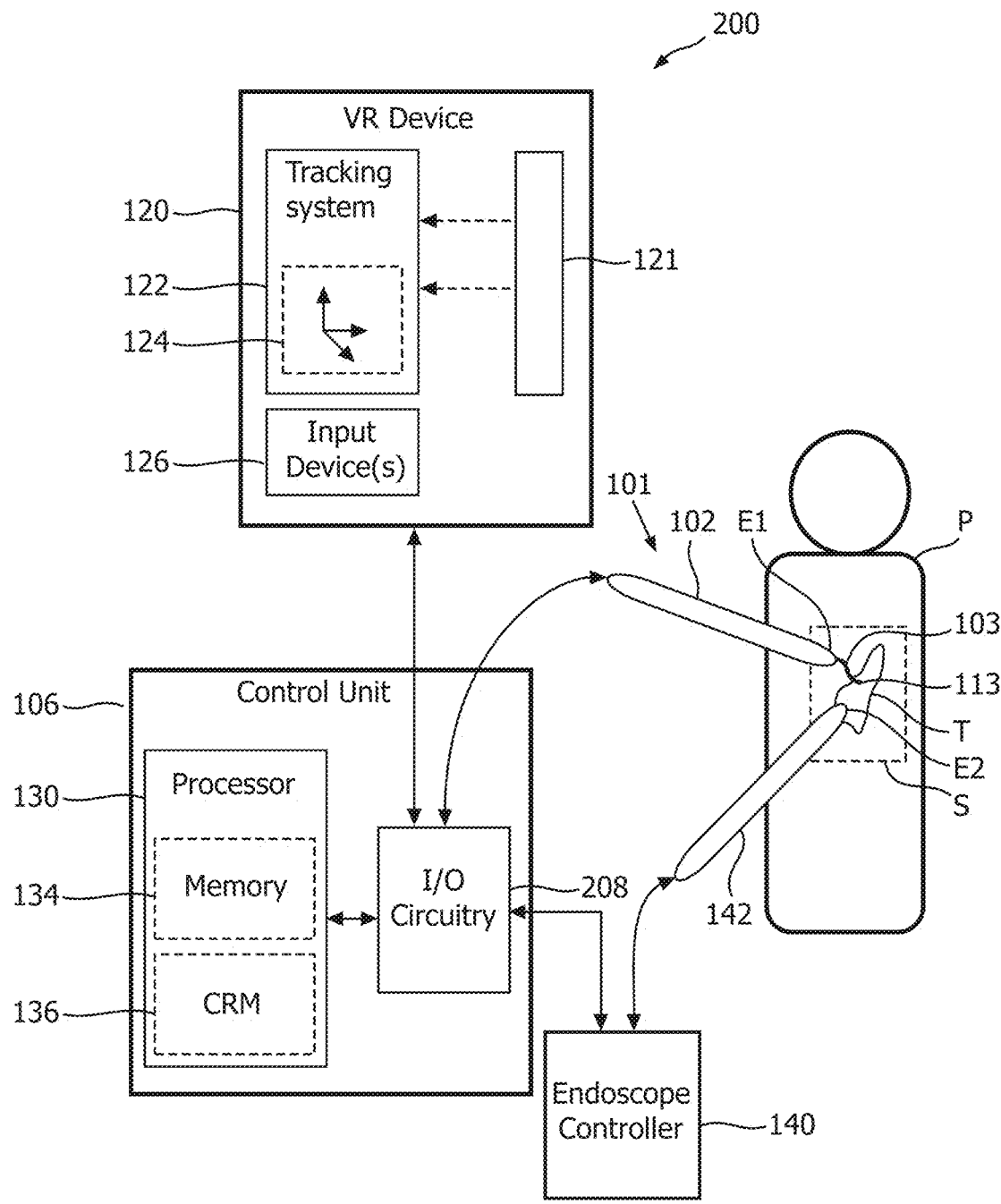
FIG. 2 is a schematic block diagram showing a surgical robot system, in accordance with an illustrative embodiment of the present invention.

FIG. 2 is a schematic block diagram showing a surgical robot system, in accordance with a representative embodiment of the present invention, including a separate imaging endoscope and corresponding endoscope controller. FIG. 2 depicts surgical robot system 200, which may be utilized for medical procedures, typically involving manipulation of surgical instruments and other tools operable by a robot at a surgical site located within a patient's body. Such medical procedures include, but are not limited to, minimally invasive cardiac surgery (e.g., coronary artery bypass grafting or mitral valve replacement), minimally invasive abdominal surgery (laparoscopy) (e.g., prostatectomy or cholecystectomy), and natural orifice translumenal endoscopic surgery, for example.

Referring to FIG. 2, in the depicted embodiment, the surgical robot system 200 is similar to the surgical robot system 100 in that it includes at least one robot 101, a control unit 106, and a VR device 120. The robot 101 is configured to operate one or more end-effectors to be positioned at a surgical site S within a patient P, including at least one instrument 113, such has a surgical tool for performing an internal surgical procedure. Internal surgical procedures may include minimally invasive surgeries or natural orifice surgeries, for instance, involving an anatomical target T within the surgical site S, examples of which are mentioned above.

In addition, the surgical robot system 200 includes endoscope controller 140 configured to control endoscope 142, which is separate from the robot 101. The endoscope 142 is an image acquisition device, similar in functionality to the at least one image acquisition device 112 discussed above with reference to FIG. 1. The endoscope 142 is configured to acquire live images at the surgical site S. "Endoscopy" means looking inside and typically refers to looking inside the body for medical reasons using an endoscope, such as the endoscope 142, which is inserted directly into the body and/or organ. The VR device 120 is configured to display the live images acquired by the endoscope 142 on the VR display unit 121 to be viewed by the user, and to detect tracking data using a VR tracking system 122 that captures the user's movements (responsive to the displayed images) via one or more motion sensing circuits, indicated by representative motion sensor 124, as discussed above.

In various embodiments, the endoscope 142 may include a rigid or flexible tube, a light delivery system to illuminate the organ or object under inspection (e.g. the light source is normally outside the body and the light is typically directed via an optical fiber system), a lens system transmitting the image from the objective lens to the viewer, typically a relay lens system in the case of rigid endoscopes or a bundle of fiber optics in the case of a fiberscope. Also contemplated are videoscopes, with no eyepiece, in which a camera transmits images to a screen for image capture. Also, in various embodiments, the endoscope 142 may be a stereoscopic endoscope, for example, that image data enabling display of apparent three-dimensional images, e.g., on the VR display unit 121.

In the depicted embodiment, the robot 101 has a rigid proximal portion 102 to be positioned at a first entry point E1 in the body of the patient P, and a flexible distal portion 103 to be positioned at a surgical site S within the patient P. The endoscope 142 includes a sheath to be positioned at a second entry point E2 in the body of the patient P. In various embodiments, the endoscope 142 may include multiple channels, one of which provides the image acquisition, and at least one other of which enables entry and control of another instrument, such as a medical instrument or manipulator, and/or a light source for illuminating the surgical site S, to be controlled by the endoscope controller 140.

The control unit 106 is configured to control and otherwise coordinate overall operations of the surgical robot system 200, including control and coordination of the robot 101 and the endoscope 142. The control unit 106 includes I/O circuitry 208, which differs from the I/O circuit 108 in that it has an additional interface(s) for communicating with the endoscope controller 140. Thus, the processor 130 is generally configured to receive the acquired live images from the endoscope 142 via the endoscope controller 140 and the I/O circuitry 208, and to process and store the acquired live images, e.g., in the memory 134 and/or the CRM 136, so that the processor 130 is able to build a database essentially visually mapping interior portions of the patient P traversed by the endoscope 142. This database may be used subsequently to determine a path to the target T, once the target T has been selected, as discussed below. The processor 130 transmits the acquired live images to the VR device 120 via the I/O circuitry 208 for display on the display unit 121. In alternative configurations, the acquired live images may be transmitted to the VR device 120 from the I/O circuitry 208 upon receiving the acquired live images by the I/O circuitry 108 from the endoscope controller 140, without any imaging processing performed by the processor 130.

The processor 130 is further configured to receive tracking data to determine by the VR tracking system 122 from the VR device 120 via the I/O circuitry 208, and to process the determined tracking data to select a target (e.g., the target T) at the surgical site S within the patient P. The processor 130 is further configured to determine a path for the one or more end-effectors of the robot 101, e.g., including the illustrative instrument 113, to reach the selected target T based upon the acquired live images and the processed determined tracking data. The processor 130 transmits robot control signals to the robot 101 via the I/O circuitry 208 to move the one or more end-effectors to the selected target T along the determined path.

Accordingly, the I/O circuitry 208 receives the acquired live images from the image acquisition device 112 via the endoscope 142 and the endoscope controller 140, and provides the acquired live images to the processor 130 and/or to the VR device 120 (either directly or forwarded from the processor 130 after image processing) for display on the display unit 121. The I/O circuitry 208 also receives the input data (including tracking data) from the VR device 120, which it provides to the processor 130, and sends robot control signals determined by the processor 130 in response to the tracking data to the robot 101.

Referring to the VR device 120 (shown in FIGS. 1 and 2), the display unit 121 includes one or more displays that may be co-located near the user. For example, referring to FIGS. 3 and 4A, when the VR device 120 is implemented as a HMD device, the display unit 121 may be attached to the front of a head piece 220, directly in front of eyes of a user 333, like goggles. The display unit 121 is configured to display live images of the surgical site S, as discussed above, and the user moves his or her head and/or eyes observing the live images displayed on the display unit 121 and tracking a target for selection, thus simulating actual surgical procedures in which the surgeon moves his or her head and/or eyes to observer the surgical site and perform the procedure. When the image acquisition device 112 provides stereoscopic images, the live images displayed on the display unit 121 may appear to be three-dimensional. In an embodiment, the display unit 121 may also display preoperative images. Thus, the images from the at least one image acquisition device 112 are captured and displayed in the HMD device.

Figure 3:
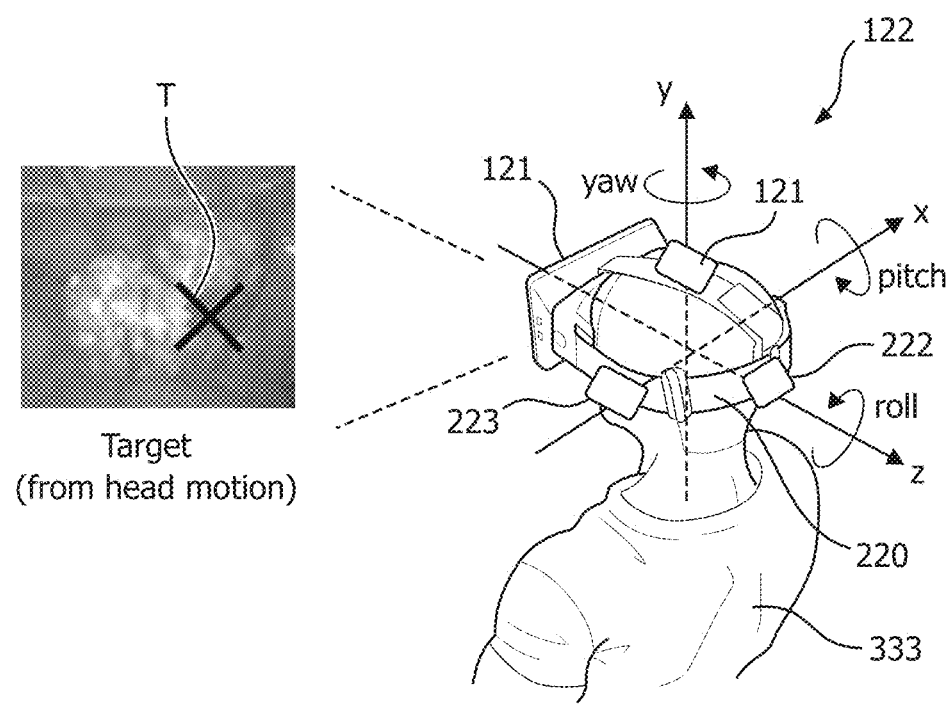
FIG. 3 is a schematic diagram showing a head mounted display (HMD) device with head-tracking capability as part of a surgical robot system, in accordance with an illustrative embodiment of the present invention.

Referring to FIG. 3, in particular, which is a schematic diagram showing an HMD device with head-tracking capability as part of the surgical robot system 100 or 200, in accordance with an illustrative embodiment of the present invention, the VR tracking system 122 of the HMD device is configured to generate tracking data based on the motion of the user's head. For example, a stereoscopic endoscope acquires live images of the surgical site S, and the live images are displayed on the HMD device. The stereoscopic endoscope may be the image acquisition device 112 controlled by the robot 101 and the control unit 106 or the endoscopic 142, not attached to the robot 101 and controlled by the separate endoscopic controller 140, discussed with reference to FIG. 2.

The user 333 may activate the head-tracking mode using the input device 126 (e.g., a foot pedal, a push button or a voice command). The VR tracking system 122 tracks the motion of the user's head, and sends tracking data to the processor 130 to compute motion to select the target T on a screen or viewer (not shown) on the back face of the display unit 121 in the HMD device. For example, the motion computation may be performed using planar head motion in the image plane. In this case, the at least one motion sensor 124 may comprise one or more accelerometers that measure head motion of the user 333. More particularly, in the depicted embodiment, the VR tracking system 122 includes three accelerometers, first accelerometer 221 for measuring head motion around a y-axis (indicating yaw), second accelerometer 222 for measuring head motion around a z-axis (indicating roll), and third accelerometer 223 for measuring head motion around an x-axis (indicating pitch). The VR tracking system 122 translates the axial motions respectively detected by the first through third accelerometers 221-223 into tracking data, which is provided to the processor 130 via the I/O circuitry 108 as input data.

The processor 130 is then able to identify or select the target T by processing the tracking data to determine the angle of the user's head in relation to the display unit 121 (and the live images displayed thereon), where the head angle indicates the region or point of the live image, which constitutes the target T within the surgical site S, at which the user 333 is looking. Once the user 333 is satisfied with the position of the target T in the surgical field S on the display unit 121, an acknowledgement signal may be sent to the processor 130 in the control system 106 (e.g., via a foot pedal, a push button or a voice command). The processor 130 may assign (or address) coordinates in two or three dimensions corresponding to the selected target T. Knowing the location of the entry point E in the body of the patient P and the coordinates of the selected target T, together with the database of acquired live images from the image acquisition device 112 (or the endoscope 142), the processor 130 is able to determine a path (or vector(s)) for the at least one instrument 113 operable by the robot 101 to reach the selected target T. An example of determining such a path for a robotically controlled instrument to reach a target in a surgical site of a patient is provided by Popovic et al., U.S. Pat. No. 8,934,003 (Jan. 13, 2015), which is hereby incorporated by reference. The processor 130 is then able to transmit robot control signals to the robot 101 causing the robot 101 to guide a distal end of the at least one instrument 113 to the target T via the determined path. That is, the control system 106 issues commands to robot 101 to move to the position of the selected target T. The requited motion of each joint of the robot 101 is implemented by the processor 130 using methods known in art. For example, the robot 101 may utilize visual servoing methods known in art.

Figure 4A:
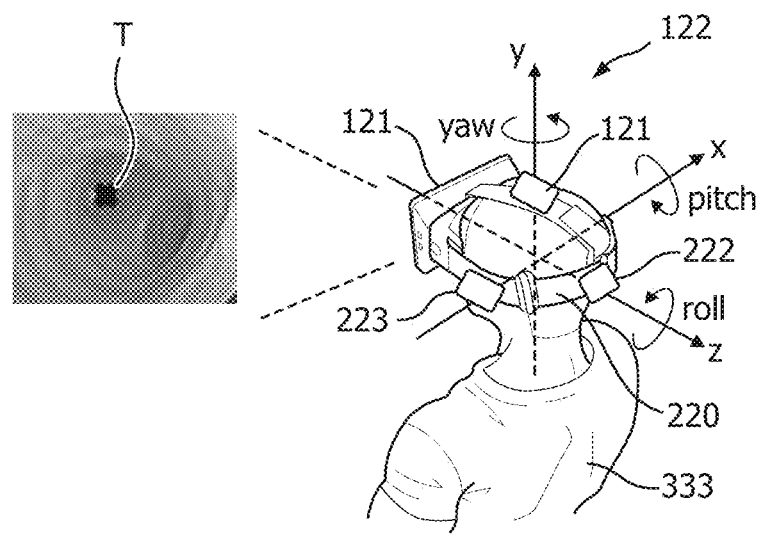
FIG. 4A is a schematic diagram showing an HMD device as part of a surgical robot system, in accordance with an illustrative embodiment of the present invention.

Referring to FIG. 4A, the VR tracking system 122 of the HMD device is configured to generate tracking data based on the motion of the user's head, as discussed above with reference to FIG. 3. Again, the user 333 may activate the head-tracking mode using the input device 126 (e.g., a foot pedal, a push button or a voice command). The at least one motion sensor 124 may comprise one or more accelerometers (first through third accelerometers 221-223) that measure head motion of the user 333 around respective axes. The VR tracking system 122 translates the axial motions into tracking data, which is provided to the processor 130 via the I/O circuitry 108 as input data. The processor 130 is then able to identify or select the target T by processing the tracking data to determine the angle of the user's head in relation to the display unit 121 (and the live images displayed thereon), as discussed above.

Figure 4B:
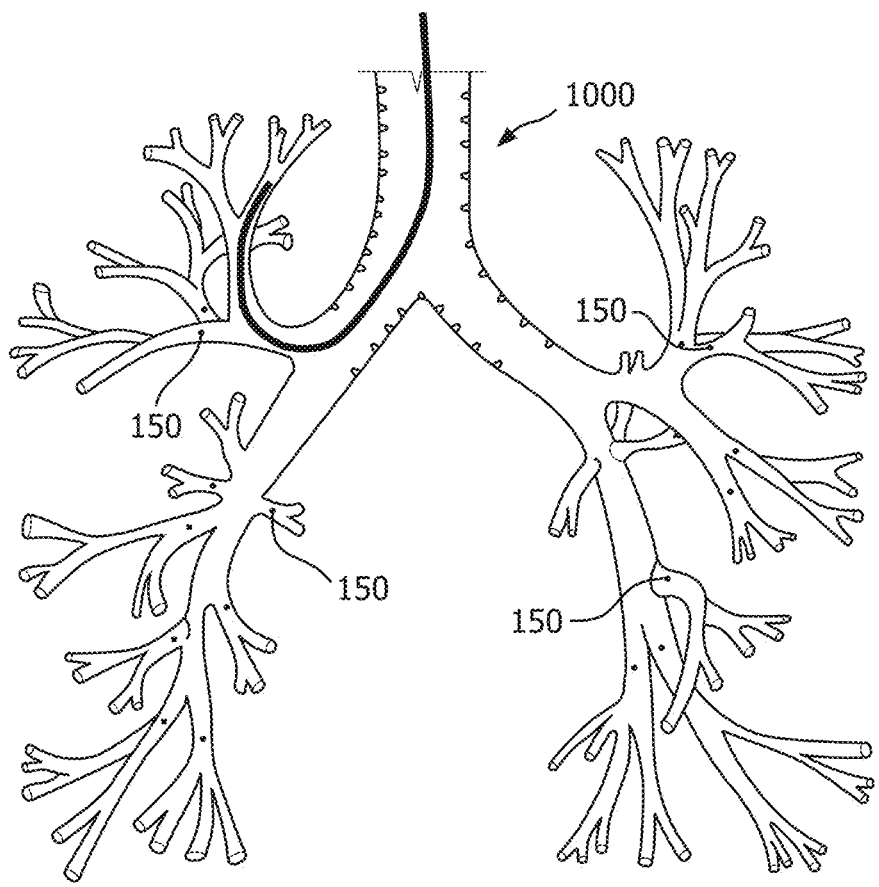
FIG. 4B is a schematic diagram showing a portion of a snake-like or catheter-like robot for traversing natural orifices using an HMD device, in accordance with an illustrative embodiment of the present invention.

FIG. 4A, however, specifically depicts operation when the image acquisition device 112 includes a forward-looking camera as part of a robot, which may be a multi-link or concentric arc robot holding a rigid endoscope for minimally invasive surgery or snake-like or catheter-like robot 1000, as shown in FIG. 4B, for traversing natural orifices 150 (e.g., bronchoscopy). In the depicted embodiment, the user 333 may perform a virtual walk-through of the anatomy, and the robot 1000 is following along this path. The target selection and motion are continuous. In other words, the processor 130 is configured to process forward-looking images from the forward-looking camera, to process the determined head-tracking and/or eye-tracking data from the HMD in a continuous travel mode, and to transmit the robot control signals to cause the robot to move the forward-looking camera in the continuous travel mode in the patient based upon the forward-looking images and the determined head-tracking or eye-tracking data.

As mentioned above, the motion sensor 124 of the VR device 120 may an eye-tracking system including two backward facing cameras for detecting movement of the user's eyes. This is may be implemented, for example, when the VR device 120 is an HMD device, as discussed above, including a head piece 220 worn by the user 333 that includes the display unit 121 and the two backward facing cameras, mounted either on the head piece 220 adjacent the display unit 121 or on a back face of the display unit 121 itself.

Figure 6:
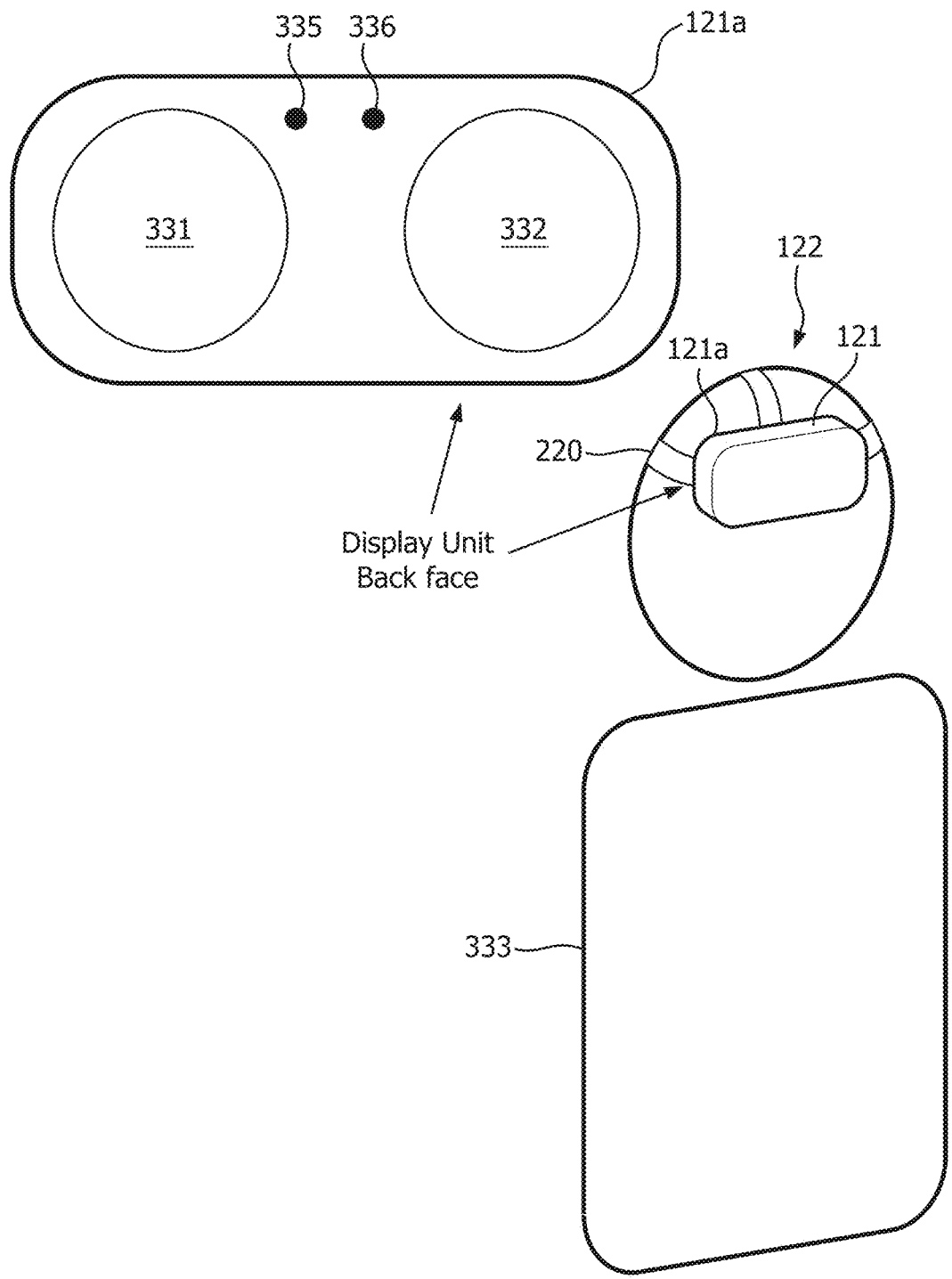
FIG. 6 is a schematic diagram showing an HMD device with eye-tracking capability as part of a surgical robot system, in accordance with an illustrative embodiment of the present invention.

FIG. 6 is a schematic diagram showing an HMD device with eye-tracking capability as part of the surgical robot system 100 or 200, in accordance with an illustrative embodiment of the present invention. Referring to FIG. 6, the back face of the display unit 121 on the head piece 220 worn by the user 333 has a binocular screen or viewer comprising a left eyepiece 331 and a right eyepiece 332, which are substantially aligned with the left and right eyes of the user 333, respectively. The back face of the display unit 121 further includes two backward facing cameras, indicated as left eye tracker 335 and right eye tracker 336, which are configured particularly to follow the irises of the user's eyes. The target selection is then performed using an eye-tracking system integrated in the HMD device and/or the processor 130. The eye movements are mapped on the left and right eyepieces 331 and 332, respectively, and/or to the surgical site S by the processor 130, and the target T is moved, accordingly. Thus, the tracking signals of the VR tracking system 122 are referred to as eye-tracking signals. In an alternative configuration, the back face of the display unit 121 may include a single (monocular) screen or viewer for displaying the live images. However, there may still two backward facing cameras, left eye tracker 335 and right eye tracker 336, to enable the eye-tracking capability.

Referring again to FIG. 1, the control unit 106 may be broadly defined herein as any controller which is structurally configured to provide one or more control commands to control the acquisition and processing of live and preoperative images related to the flexible distal portion 103 of the robot 101 at the surgical site S, and the anatomical object or target T, and utilize tracking information related to selection of the target T from the VR device 130 to determine a path to the target T and to further control the flexible distal portion 103. Generally, the I/O circuitry 108 controls communication among elements and devices external to the control unit 106. The I/O circuitry 108 acts as an interface including necessary logic to interpret input and output signals or data to/from the processor 130, the VR device 120 and the robot 101. The I/O circuitry 108 may include a first input configured to receive the acquired live images from the image acquisition device 112, and a first output configured to provide the acquired live images to at least one of the processor 130 and the VR device 120 ultimately for display. The I/O circuitry 108 may further include a second input configured to receive determined input data, including tracking data, from the VR device 120, a second output configured to provide the determined input data to the processor 130, which processes the input data to identify and select the target T in response, and a third output configured to provide robot control signals to the robot 101.

The processor 130 may perform the described functions and operations using a combination of hardware, software and firmware. The processor 130 is configured to process medical imagery (e.g. from the image acquisition device 112 or an external medical imagery device) related to the flexible distal portion 103 of the surgical robot 101 at the surgical site S to register the flexible distal portion 103 with corresponding anatomy at the surgical site S. The processor 130 may be configured to process additional positional tracking information of the rigid proximal portion 102 of the surgical robot 101 from a position tracking system (not shown) to determine motion of the rigid proximal portion 102. The position tracking system, which is separate from the tracking system 120, may be one or more of an optical tracking system, mechanical tracking system, and electromagnetic tracking system, as would be appreciated by those skilled in the art. A sensor or tag (e.g. light emitting diodes (LEDs), passive markers, reflective markers, etc.) may be included at the rigid proximal portion 102 of the surgical robot 101 to cooperate with the position tracking system. In an embodiment, a position compensation mode may be provided, according to which the processor 130 is configured to generate motion compensation signals for the flexible distal portion 103 of the surgical robot 101 based upon the determined positions and motion of the rigid proximal portion 102.

With additional reference to FIGS. 2-4, the robot 101 is dexterous and inserted into the patient through the entry point E. The rigid proximal portion 102 may be hand-held. This rigid proximal portion 102 pivots around the entry point E ("pivot point"). The flexible distal portion 103 moves inside the patient P without injuring the entry point E.

In a position compensation mode, an image related to the flexible distal portion 103 is taken using the image acquisition device 112 or the external medical imagery device, such as X-ray (or cone-beam CT, US, endoscope, etc.) as discussed above. The shape and pose of the flexible distal portion 103, and/or registration within the surgical site S, is determined using various approaches known in the art, such as real-time tracking of surgical tools relative to a pre-operative surgical plan and intra-operative images involving an image-based registration and tool tracking registration. That is, because the robot 101, with or without the endoscope 142, introduces an additional coordinate system, alignment (position and orientation) of the robot 101 with some desired frame of reference is difficult to guarantee and maintain because it is positioned with workspace and motion constraints. Registration addresses the issue of misalignment of disparate coordinate systems so that the same alignment need not be performed mentally by clinicians. Registration of the robot 101 enables capabilities such as registration of preoperative images to a live endoscope feed, which can help with localization of anatomical targets. The preoperative images may include 3D images such as those obtained via computed tomography (CT), ultrasound, magnetic resonance imaging (MRI), positron emission tomography (PET), single-photon emission computed tomography (SPECT) and the like.

A variety of methods exist to register a surgical robot 101 to the workspace it is in. Registration can be performed by matching features visible in the live view of the image acquisition device 112 with corresponding features known through other ways such as a preoperative CT. An example of image-based registration and tool tracking registration in endoscopic surgery is described by Popovic, U.S. Pat. No. 9,095,252 (Aug. 4, 2015), which is hereby incorporated by reference. Registration of the flexible distal portion 103 may include: 1) acquiring an interoperative image of the flexible distal portion 103 of the robot 101 and the surrounding anatomy (e.g. from an external medical imagery device, discussed above) and performing the registration; or 2) acquiring an image of the surrounding anatomy from the flexible distal portion 103 of robot 101 (e.g. from the image acquisition device 112, such as a camera or ultrasound transducer).

In practice, the discussed control processes may be implemented by modules that are embodied by any combination of hardware, software and/or firmware installed on any platform (e.g., a general computer, application specific integrated circuit (ASIC), etc.). Furthermore, processes may be performed by the processor 130 of control unit 106.

Embodiments of the invention may also be directed to a non-transitory computer-readable storage medium 136 having stored therein machine readable instructions configured to be executed by the processor 130 to control the surgical robot system 100 including the surgical robot 101 having the rigid proximal portion 102 to be positioned at an entry to the body of the patient P and the flexible distal portion 103 to be positioned at a surgical site S within the patient P. The corresponding machine readable instructions are configured to perform a method 500.

Figure 5:
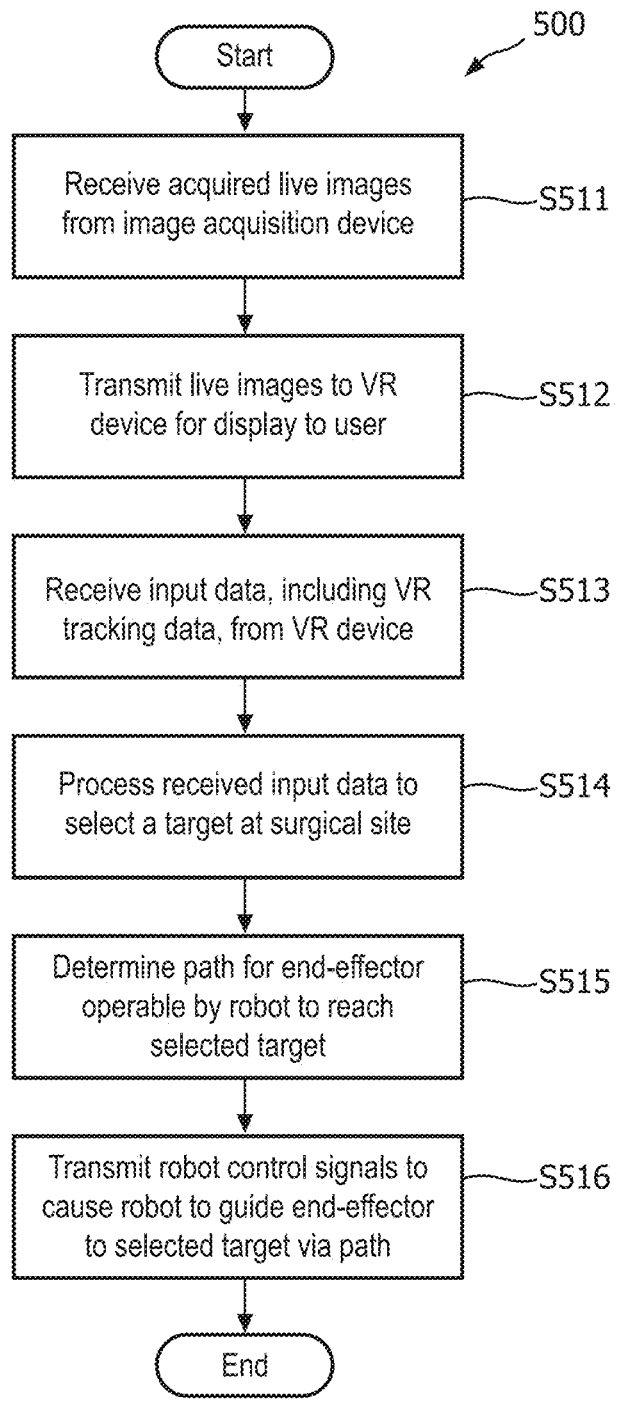
FIG. 5 is a flowchart showing a method of controlling a surgical robot system, in accordance with an illustrative embodiment of the present invention.

FIG. 5 is a flowchart showing operations of a representative embodiment of a method 500 for control and guidance of a surgical robotic system and may be implemented, for example, by the processor 130. For purposes of illustration, it will be assumed that the method 500 is performed by the version of surgical robot system 100 depicted in FIG. 1, although the method may substantially apply to alternative configurations, including surgical robot system 200, without departing for the scope of the present teachings.

Referring to FIG. 5, acquired live images are received in operation 5511 from an image acquisition device. The live images may be acquired, for example, by one or more cameras on a distal portion of the robot. The live images may be still images or video, and show the surgical site. In an alternative embodiment, the images may be acquired by an endoscope under control of the robot controller or a separate endoscope controller. In operation 5512, the live images (or live image data) are transmitted to a VR device, such as an HMD device, where the live images may be displayed to the user. Image processing may be performed on the live images prior to transmitting the live images to the VR device. When the VR device is an HMD device, for example, the live images may be displayed on a display screen or viewer in an HMD head piece. Alternatively, the live images may be displayed on a separate display unit, such as a computer monitor, located at a fixed position within view of the user. The processor may also augment the acquired live images for transmission to the VR device with visual indicators, such as direction of motion, target location, robot position, and the like.

Input data are received from the VR device in operation 513, where the input data include tracking data indicating detected motions of the user. For example, when the VR device is an HMD device, the detected motion may be head motion or eye movement of the user wearing an HMD head piece. The HMD head piece may include sensors for detecting such motion, as discussed above. The motion is translated into tracking data by a VR tracking system in the VR device and transmitted, e.g., to the processor. Alternatively, raw motion data may be transmitted to the processor, which in turn translates the raw motion data into tracking data. Other input data may include commands entered by the user, such as movement of a cursor for highlighting features of the displayed live images on the display (e.g., identifying a selected target), an acknowledgement signal confirming a selected target, and an activation signal activating they type of tracking mode, such as a head-tracking mode or an eye-tracking mode.

In operation 514, the input data received from the VR device is processed to select a target at the surgical site in the patient. Once a target is selected, a path is determined in operation 515 for an end-effector (or multiple end-effectors) operable by the surgical robot to reach the selected target based upon the live images and the processed determined input data. Robot control signals are then transmitted in operation 516 to cause the robot to guide the end-effector to reach the selected target at the surgical site via the determined path. Throughout discussion of FIG. 5, the term "transmitted" refers to sending by any mode of signal communication, including through cables or conductors and/or through wireless communication.

While various embodiments have been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A control unit for a surgical robot system, including a robot configured to operate at least one end-effector in a surgical site of a patient, the control unit comprising:

a processor configured to:
  transmit acquired images of a patient, received from at least one image acquisition device, to a virtual reality (VR) device for display on a viewer of display unit;
  receive input data from the VR device, the input data including tracking data from a VR tracking system of the VR device based on a user's response to the acquired images of the patient displayed on the viewer of the display unit of the VR device;
  process the input data received from the VR device and the acquired images to determine or select a path for the at least one end-effector operable by the robot;
  transmit robot control signals to cause the robot to guide the at least one end-effector according to the determined path.

2. The control unit according to claim 1, wherein the VR device is a head mounted display (HMD) device comprising a head piece worn by the user.

3. The control unit according to claim 2, wherein the VR tracking system comprises a head-tracking system; and
  wherein the processor is further configured to process head-tracking data from the head-tracking system to determine or select the path, the head-tracking data corresponding to head movements of the user.

4. The control unit according to claim 2, wherein the VR tracking system comprises an eye-tracking system; and
  wherein the processor is further configured to process eye-tracking data from the eye-tracking system to determine or select the path, the eye-tracking data corresponding to eye movements of the user.

5. The control unit according to claim 1, wherein the at least one end-effector operable by the robot comprises at least one of a surgical tool and an endoscopic camera.

6. The control unit according to claim 1, further comprising input/output (I/O)
  circuitry including:
    a first input configured to receive the acquired images from the image acquisition device;
    a first output configured to provide the acquired images to at least one of the processor and the VR device;
    a second input configured to receive the input data from the VR device; and
    a second output configured to provide the robot control signals to the robot.

7. The control unit according to claim 1, wherein the display unit of the VR device provides a movable cursor for highlighting features of the acquired images displayed on the viewer.

8. The control unit according to claim 1, wherein the processor is further configured to process an acknowledgment signal from an input device to confirm the determined or selected path.

9. The control unit according to claim 2, wherein the processor is further configured to process an activation signal from an input of the HMD to activate one of an eye-tracking mode and a head-tracking mode that includes determination of eye movements and corresponding eye-tracking data or head motion and corresponding head-tracking data, respectively.

10. The control unit according to claim 1, wherein the processor is further configured to augment the acquired images for transmission to the VR device with visual indicators.

11. The control unit according to claim 9, wherein the at least one image acquisition device includes a forward-looking camera operable by the at least one robot; and
wherein the processor is further configured to process forward-looking images from the forward-looking camera, process the determined eye tracking or head tracking data from the HMD in a continuous travel mode, and transmit the robot control signals to cause the robot to move the forward-looking camera in the continuous travel mode based upon the forward-looking images and the determined eye-tracking or head-tracking data.

12. A surgical robot system comprising:
  a robot configured to operate at least one end-effector positioned at a surgical site within a patient;
  at least one image acquisition device configured to acquire images at the surgical site;
  a virtual reality (VR) device configured to display the acquired images and determine tracking data provided by actions of a user via the VR device; and
  a control unit comprising:
    input/output (I/O) circuitry configured to receive the acquired images from the at least one image acquisition device, provide the acquired images to the VR device for display, receive the determined tracking data from the VR device, and provide robot control signals to the robot; and
    a processor configured to:
    transmit the acquired images, received from the at least one image acquisition device via the I/O circuitry, to the VR device;
    process the determined tracking data from the VR device and the acquired image to select or determine a path for the at least one end-effector operable by the robot; and
    transmit the robot control signals to the robot to move the at least one instrument according to the determined or selected path.

13. The surgical robot system according to claim 12, wherein the VR device is a head mounted display (HMD) worn by the user, and
  wherein the tracking data comprises at least one of head-tracking data corresponding to head motion of the user detected by the HMD, and eye-tracking data corresponding to eye movements of the user detected by the HMD.

14. The surgical robot system according to claim 12, further comprising an input device coupled to the control unit, wherein the processor is further configured to process an acknowledgment signal from the input device to confirm the determined or selected path.

15. The surgical robot system according to claim 14, wherein the processor is further configured to process an activation signal from the input device to activate one of a head-tracking mode that includes the detection of the head motion by the HMD or an eye-tracking mode that includes the detection of the eye movements by the HMD.

16. The surgical robot system according to claim 12, wherein the at least one image acquisition device comprises a stereoscopic endoscope.

17. The surgical robot system according to claim 12, wherein the robot comprises a rigid proximal portion coupled to a flexible distal portion including the at least one end-effector.

18. A non-transitory computer-readable storage medium storing machine readable instructions executable by a processor to operate a surgical robot system, including at least one robot configured to operate at least one end-effector to be positioned at a surgical site within a patient, at least one image acquisition device configured to acquire images at the surgical site, and a head-mounted display (HMD) device to be worn by a user and configured to display the acquired images and to determine at least one of motion of the user's head or movement of the user's eyes, the non-transitory computer readable medium comprising:

transmitting code for causing transmission of the acquired images, received from the at least one image acquisition device, to the HMD device;

processing code for processing determined at least one of head-tracking data and eye-tracking data from the HMD device and the acquired images to select or determine a path at the surgical site for the at least one end-effector operable by the robot; and robot control code for causing transmission of the robot control signals to the robot to move the at least one end-effector according to the selected or determined path at the surgical site.

19. The non-transitory computer-readable storage medium according to claim 18, further comprising acknowledgement code for processing an acknowledgment signal from an input device to confirm the selected or determined path by a user.

20. The non-transitory computer-readable storage medium according to claim 18, further comprising activation code for processing an activation signal from an input device to activate a head-tracking mode that includes sensing of head motion by the HMD device or an eye-tracking mode that includes sensing of eye movement by the HMD device.

21. The non-transitory computer-readable storage medium according to claim 18, further comprising augmenting code for augmenting the acquired images for transmission to the HMD device with visual indicators.

22. The non-transitory computer-readable storage medium according to claim 18, further comprising forward-looking image code for:

processing forward-looking images from a forward-looking camera associated with one of the end-effectors controllable by the robot;

processing the determined head-tracking data from the HMD in a continuous travel mode; and transmitting the robot control signals to move the at least one robot in the continuous travel mode at the surgical site based upon the forward-looking images and the determined head-tracking data.

\* \* \* \* \*